United States Patent [19]
Constantz et al.

[11] Patent Number: 6,002,065
[45] Date of Patent: *Dec. 14, 1999

[54] KITS FOR PREPARING CALCIUM PHOSPHATE MINERALS

[75] Inventors: Brent R. Constantz, Los Gatos; Mark T. Fulmer, Santa Clara; Bryan M. Barr, Sunnyvale, all of Calif.

[73] Assignee: Norian Corporation, Cupertino, Calif.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/820,126

[22] Filed: Mar. 19, 1997

Related U.S. Application Data

[60] Continuation of application No. 08/221,646, Apr. 1, 1994, Pat. No. 5,820,632, which is a division of application No. 07/918,233, Jul. 23, 1992, Pat. No. 5,336,264, which is a continuation-in-part of application No. 07/722,880, Jun. 28, 1991, abandoned, which is a continuation-in-part of application No. 07/650,462, Feb. 4, 1991, abandoned, which is a continuation of application No. 07/393,579, Aug. 14, 1989, Pat. No. 5,129,905, which is a continuation-in-part of application No. 07/358,716, May 30, 1989, Pat. No. 5,047,031, which is a continuation-in-part of application No. 07/183,770, Apr. 20, 1988, Pat. No. 4,880,610.

[51] Int. Cl.[6] .................................................. A61F 2/28
[52] U.S. Cl. ............................ 623/16; 623/66; 423/309; 423/315; 423/317
[58] Field of Search ..................... 623/16, 66; 423/305, 423/308, 309, 311, 315, 317

[56] References Cited

U.S. PATENT DOCUMENTS

| | | | |
|---|---|---|---|
| Re. 33,161 | 2/1990 | Brown et al. | 423/308 |
| Re. 33,221 | 5/1990 | Brown et al. | 423/308 |
| 3,873,327 | 3/1975 | Duff | 623/16 |
| 3,913,229 | 10/1975 | Driskell et al. | 32/15 |
| 4,139,599 | 2/1975 | Tomlinson et al. | 423/308 |
| 4,481,175 | 11/1984 | Iino et al. | 423/308 |
| 4,487,749 | 12/1984 | Sherif et al. | 423/309 |
| 4,518,430 | 5/1985 | Brown et al. | 106/35 |
| 4,673,355 | 6/1987 | Farris et al. | 433/218 |
| 4,684,673 | 8/1987 | Adachi et al. | 523/116 |
| 4,917,702 | 4/1990 | Scheicher et al. | 623/16 |
| 4,959,104 | 9/1990 | Iino et al. | 106/85 |
| 5,017,518 | 5/1991 | Hirayama et al. | 501/1 |
| 5,047,031 | 9/1991 | Constantz | 606/77 |
| 5,092,888 | 3/1992 | Iwamoto et al. | 623/16 |
| 5,149,368 | 9/1992 | Liu et al. | 424/602 |
| 5,152,836 | 10/1992 | Hirano et al. | 106/690 |
| 5,180,426 | 1/1993 | Sumita | 106/35 |
| 5,262,166 | 11/1993 | Liu et al. | 424/423 |
| 5,320,844 | 6/1994 | Liu | 424/422 |
| 5,322,675 | 6/1994 | Hakamatsuka et al. | 423/311 |
| 5,336,264 | 8/1994 | Constantz et al. | 623/66 |
| 5,508,342 | 4/1996 | Antonucci et al. | 524/788 |
| 5,525,148 | 6/1996 | Chow et al. | 106/35 |
| 5,536,575 | 7/1996 | Imura et al. | 428/403 |
| 5,569,490 | 10/1990 | Imura et al. | 427/212 |
| 5,820,632 | 10/1998 | Constantz et al. | 623/16 |

FOREIGN PATENT DOCUMENTS

| | | |
|---|---|---|
| 0639 366 A | 8/1983 | European Pat. Off. . |
| 0520 690 A | 6/1992 | European Pat. Off. . |
| 0543 765 A | 10/1992 | European Pat. Off. . |
| 2 693 716 | 7/1992 | France . |
| 57-70216 | 4/1982 | Japan . |
| 58-89288 | 5/1983 | Japan . |
| 59-56676 | 3/1984 | Japan . |
| 59-192365 | 9/1984 | Japan . |
| 62-193482 | 7/1987 | Japan . |
| 1-74591 | 3/1989 | Japan . |
| 1-203801 | 8/1989 | Japan . |
| 1-266235 | 10/1989 | Japan . |
| 1-279811 | 10/1989 | Japan . |
| 2-117444 | 5/1990 | Japan . |
| 2-117445 | 5/1990 | Japan . |
| 3-182585 | 7/1991 | Japan . |
| 2 248 232 A | 9/1991 | United Kingdom . |
| 2 260 977 A | 10/1992 | United Kingdom . |
| WO 90/00892 | 2/1990 | WIPO . |
| WO 95/08304 | 3/1995 | WIPO . |
| WO 95/08319 | 3/1995 | WIPO . |

OTHER PUBLICATIONS

Chohayeb, et al., "Evaluation of Calcium Phospahte as a Root Canal Sealer–Filler Material," Journal od Endodontics (Aug. 1987) vol. 13:384.

Chow, S., "The Centennial Memorial Issue of the Ceramic Society of Japan, " Ceramic Soc. Japan (1991)vol. 99954–964.

Chow,S., "Calcium Phosphate Materials: Reactor Response," Adv. Dent. Res. (Aug. 1988) vol. 2: 181–184.

Constantz, et al., "Pilot Investigations of A Calcium Phosphate Cement In a Rabbit Femoral Canla Model and A Canine Humeral Plug Model," 17th Annual Meeting of the Society for Biomaterials May 1–5 (1991).

Fukase, et al., "Setting Reaction and Compressive Strengths of Calcium Phosphate Cements," J. Dental Res. (Dec. 1990) vol.69:1852.

Le Maitre, et al., "Calcium Phosphate Cements for Medical Use: State of the Art and Perspectives of Development," Silicate Industries (1987) vol. 9—10:141.

Mirtchi: Le Maitre, "Calcium Phosphate Cements: Study of the β–Tricalcium Phosphate–Monocalcium Phosphate Dicalcium Phosphate–Calcite Cements," Biomaterials (Jul. 1991) vol. 10:475.

Mirtchi: Le Maitre, "Calcium Phosphate cements: Study of the β–Tricalcium Phosphate–Monocalcium Phosphate Dicalcium Phosphate–Calcite Cements," Bopmaterials (Mar. 1990) vol. 11:84.

(List continued on next page.)

Primary Examiner—Paul B. Prebilic
Attorney, Agent, or Firm—Bozicevic, Field & Francis; Bret Field

[57] ABSTRACT

Setting times of calcium phosphate cement compositions are enhanced by the addition of phosphate or carbonate lubricant compositions. Methods for preparing the cement compositions are provided.

10 Claims, No Drawings

OTHER PUBLICATIONS

Mirtchi, et al., "Calcium Phosphate cements: Effect of Fluorides on the Setting and Hardening of 62–Tricalcium Phosphate–Dicalcium–Phosphate–Calcite Cements," Bomaterials (Mar. 1990) vol. 11:84.

Monma et al., "Properties of Hydroxyapatite Prepared By The Hydrolysis of Triacalcium Phosphate," J. Chem. Tech. Biotech. (1981) vol. 31: 15–24.

Okazki, et al., "Crystallinity, Solubility, and Dissolution Rate Behavior of Fluoridated $CO_3$ Apatites," J. Biomedical Mat. Res. (1982) vol. 16:851–860.

Sanin et al., "Effects of Additivces on Setting Reaction of Calcium Phosphate Cement," ADDR (Jan. 15, 1992) No. 666.

KITS FOR PREPARING CALCIUM PHOSPHATE MINERALS

This application is a continuation of U.S. application Ser. No. 08/221,646 filed Apr. 1, 1994, and issued as U.S. Pat. No. 5,820,632; which application is a divisional of U.S. application Ser. No. 07/918,233 filed Jul. 23, 1992, and issued as U.S. Pat. No. 5,336,264; which application is a continuation-in-part of U.S. application Ser. No. 07/722,880, filed on Jun. 28, 1991 and now abandoned; which application is a continuation-in-part of U.S. application Ser. No. 07/650,462, filed on Feb. 4, 1991 and now abandoned; which application is a continuation of U.S. application Ser. No. 07/393,579 filed Aug. 14, 1989 and now issued as U.S. Pat. No. 5,129,905; which application is a continuation-in-part of U.S. application Ser. No. 07/358,716 filed May 30, 1989 and now issued as U.S. Pat. No. 5,047,031; which application is a continuation-in-part of U.S. application Ser. No. 07/183,770 filed Apr. 20, 1988 and now issued as U.S. Pat. No. 4,880,610; the disclosures of which applications are herein incorporated by reference.

INTRODUCTION

TECHNICAL FIELD

The field of this invention is preparation of calcium phosphate minerals for physiological applications.

BACKGROUND

Hydroxyapatite, as well as modified forms thereof, assume substantial interest and importance by virtue of the fact that hydroxyapatite is a major naturally occurring building block in bone, teeth and some invertebrate skeletons. There are many situations where bone has been broken, destroyed, degraded, become too brittle, or has been subject to other deteriorating effects. Numerous materials have been devised, as well as various forms of calcium phosphate, to act as supports, substitutes, or interfaces for repairing or replacing the naturally occurring structures. Preformed structures frequently do not bond to the remaining structure, so as to provide a weak juncture, which is subject to failure. Replacement structures, such as Co-Cr or Ti prostheses require that there be a strong bond between the bone to which the prosthetic device is joined and the prosthetic device. Efforts to provide a material which is moldable and will set in place have been subject to the problem of the large amount of blood which is normally present.

The blood creates many problems, in being able to wash away or dissolve mineral salts prior to their setting up as an insoluble mineral. Furthermore, the various components in the blood may become incorporated into the mineral, substantially changing its physical properties. On the other hand, one cannot have the mixture set up too rapidly, since one needs time to ensure the substantial homogeneity of the mixture, the ability to transfer the mixture to the site where it sets up, and frequently one may wish to mold the mixture. Therefore, the restrictions as to the rapidity of setting up and the ease of administering the mixture to a site creates severe limits on the properties of the materials which may be used. There is, therefore, an interest in developing materials which provide for optimum conditions in a variety of situations.

Relevant Literature

Patents of interest include U.S. Pat. Nos. 3,787,900; 3,913,229; 3,679,360; 4,097,935; 4,481,175; 4,503,157; 4,612,053; 4,659,617; 4,693,986; 4,843,112; 4,612,053; and 4,518,430. Other patents of interest include Reissue number 033,221. Articles of interest include Sugawara, *J. of Endodontics*, 16:162–165 (1990); Sugawara, et al., *J. of Dental Research*, 66:296 (1987); Brown and Chow, *Cements Research Progress* 1986, 351–379 (1987); Industry Week, Dec. 9, 1985, p. 76; Japanese Patent No. 89/230367; Chemical Abstracts 112, No. 26, Sect. 163, Abstract No. 240,566; Mirtchi et al., *Biomaterials* 11:83–88 (1990); Japanese Patent No. 89/234346; Chemical Abstracts, No. 20, Sect. 163, Abstract No. 185,872; Japanese Patent No. 88/115567; Chemical Abstracts 110, No. 12, Sect. 163, Abstract No. 101,875; Lemaitre et al., *Silic. Ind.* 52:141–146 (1987).

SUMMARY OF THE INVENTION

Novel calcium phosphate compositions and methods for preparing the compositions are provided, whereby a phosphate or carbonate solution is added to a formulation for producing calcium phosphate structural products providing rapid setting times, when the formulation is introduced into a physiological site. Particularly, a basic solution, e.g. hydroxide, acetate, phosphate or carbonate solution, is prepared from an alkali metal containing base to be used as a lubricant. Depending upon the strength requirements of the final product, one may vary the set time-enhancing solution to provide the improved setting time with varying effects on the ultimate compression strength.

DESCRIPTION OF THE SPECIFIC EMBODIMENTS

Methods and compositions are provided for producing bone-like materials comprising structures analogous to the naturally occurring physiologically acceptable calcium phosphate minerals, particularly hydroxyapatite, including carbonated and fluoridated derivatives. A composition for production of the calcium phosphate mineral is modified by adding to the calcium phosphate mineral formulation a basic solution, particularly an alkali metal hydroxide, acetate, phosphate or carbonate solution, as a lubricant. The addition of the solution substantially shortens setting time, so as to allow for rapid setting of the calcium phosphate mineral under physiological conditions, where frequently one encounters large amounts of blood, which can substantially deteriorate the characteristics of the final product. By varying the basic solution composition, one may also vary the ultimate strength of the final product.

Depending upon the nature of the application, the final strength required will vary. For example, high strength is not required, where the composition acts as a filler, such as a dental implant, as a periodontal pocket filler. By contrast, high strength is required for an injected prosthetic implant, a prophylactic injection to augment weak osteoporotic bone, as a bone defect filler where the bone is weight-bearing, or in many instances, where the composition may be used for adherence or holding a damaged structure in place while healing takes place.

In one aspect, the calcium phosphate composition which finds particular use in the subject application is described in U.S. application Ser. No. 558,890, filed Aug. 27, 1990. This composition is then mixed with the phosphate or carbonate solution as the lubricant, so as to begin setting. The mixture is substantially homogenized to ensure uniform dispersion and then may be used as appropriate. Usually, the mixing will require not more than about 1 to 3 minutes, so as to ensure that the mixture is still flowable and can be administered by means of a syringe or other device.

The solution serving as the lubricant will preferably have alkali metal hydroxide, acetate, phosphate or carbonate, particularly sodium, more particularly sodium phosphate or carbonate, at a concentration in the range of about 0.01 to 2 M, particularly 0.05 to 0.5 M, and at a pH in the range of about 6–11, more normally about 7–9, preferably 7–7.5.

The calcium phosphate mineral composition will be described first. The composition is formed in substantially two stages: a first stage which involves mechanical intimate mixing and milling of a calcium source, e.g., tetracalcium phosphate, tricalcium phosphate, calcium carbonate, or calcium oxide, and a phosphoric acid source substantially free of uncombined water, desirably having at least 2 protons per phosphate and not more than about 1 water of hydration per molecule, and, in addition other optional additives; and a second stage which involves mixing with water in the case of a dry seed, or mixing with a gel or colloid, in the case where the additive is a gel or a colloid, and optionally other additives to provide the final product, which sets up to a calcium phosphate mineral, e.g., an hydroxyapatite, having desirable mechanical properties.

The first stage involves the mechanical mixing of the primary calcium sources. The acidic neutralizing phosphate source will be free of uncombined water and may be orthophosphoric acid crystals or monocalcium phosphate monohydrate $Ca(H_2PO_4)_2 \cdot H_2O$ or other calcium phosphate acid source by itself or in combination e.g., monetite. Calcium sources present will include counterions, such as a source of carbonate, e.g., calcium carbonate, or a source of phosphate, e.g., tetracalcium phosphate or tricalcium phosphate, a base, such as calcium oxide or calcium hydroxide, a source of fluoride, such as calcium fluoride, or the like. The ratio of calcium to phosphate will provide for stoichiometries ranging from 1.1:1 to 2:1, allowing preferential formation of a number of stable compounds, including monetite, brushite, octacalcium phosphate, calcium-deficient hydroxyapatite, stoichiometric hydroxyapatite (1.67:1), or mixtures of the aforementioned minerals, in addition to various metastable amorphous calcium phosphates. By controlling the calcium-to-phosphate ratio, and hence final cement composition, it will be possible to tailor the resorption rate of the cement when administered into the body. The resorption rates will vary from as little as 2 weeks to as much as 48 months.

The reaction of calcium oxide with the acidic phosphate source results in an exothermic reaction. Where the mixture is to be used to set in situ for a bone replacement, high temperatures are undesirable. Desirably, the temperature produced should be below a pain inducing temperature, generally less than 60° C. and more desirably less than a protein denaturing temperature, generally less than 42° C. Generally, the amount of calcium oxide or calcium hydroxide will range from about 0 to 50 weight percent, more usually from about 0 to 30 weight percent, and preferably from about 5 to 15 weight percent of dry weight.

Calcium carbonate provides for some neutralizing capability and substantial buffering capability (e.g., $HCO_3$), but results in the production of carbon dioxide. The gas must be expressed and can result in building up of high pressures in a closed milling system. Therefore, when using calcium carbonate or other carbonate, it is essential that means be provided for releasing the pressure or using a system capable of maintaining elevated pressures. Usually, the calcium carbonate will be present in from about 0 to 70 weight percent, more usually from about 0 to 40 weight percent, and preferably from about 2 to 18 weight percent of dry weight.

The tetracalcium or tricalcium phosphate may typically be in major proportion in the mixture, generally ranging from about 55 to 75 weight percent, more usually from about 60 to 70 weight percent of dry weight.

The acid source will generally be about 15 to 35 weight percent, more usually 15 to 25 weight percent.

The source of fluoride will generally be present, if at all, in relatively small amounts, generally ranging from about 0 to 4 weight percent, more usually from about 2 to 4 weight percent, preferably from about 3 to 4 weight percent of dry weight.

The dry ingredients are combined, particularly as powders or small particles, the particular size of the particles not being crucial to this invention, but certain ranges being preferred. Generally, the particles will be smaller than about $500\mu$, more usually smaller than about $250\mu$ and may range from about 50 Angstroms to $200\mu$ on the average. Since small amounts of fine powder will skew the average size, it should be understood that in referring to the average size, the intent is those particles contributing to at least about 80 weight percent of the component, usually at least about 90 weight percent.

Raw material particle size prior to milling or mechano-chemical mixing may be varied in order to choose the particular chemical reaction paths within the milling jar. By decreasing powder size, effective surface area is increased, allowing the initial composition of the reaction products to be altered, consequently affecting the final powder product composition, and hence mechanical, physical, and mixing properties.

Small amounts of organic polymers, particularly proteins, substantially anhydrous, may be included in the mixture prior to completion of the mechanical mixing. A list of proteins is found in the parent application, which is incorporated herein by reference, and will also be provided herein. The amount of additive will generally be from about 1 to 40 weight percent, more usually, 1 to 25 weight percent of the inorganic materials. Desirably, the polymer is added to the inorganic materials before milling, mixed while substantially retaining the bulk of the additive and then introduced into the milling device. Since the bulk will usually be substantially diminished during milling, media should be removed accordingly.

The particular manner in which the various dry ingredients are combined is not critical to this invention, so long as intimate mixing occurs, partial reaction may proceed between the ingredients without complete reaction. Alternatively, it may be desirable to mix or mill the calcium sources by one process and combine them with the phosphate sources and/or phosphate additive via another mixing or milling process. Techniques which may be used include amalgamator (wig-l-bug), ball milling, Brabender mixing, blender, rolling between one or two rollers in a flexible container, or the like. Various equipment may be used, including ball mills, mortar and pestle, planetary mills, centrifugal mills, mechanofusion systems, air pulverizers, jet mills, vibratory mills, colloid mills, attrition mills, disc mills, and the like.

The course of the mixing can be monitored by taking aliquots and testing to see whether the aliquots provide for the desired physical properties when mixed with an aqueous medium, by stopping the mixing when undue caking occurs, or by compositional determination via XRD or FTIR. Depending upon the nature of the mixing, the efficiency of the mixing, the size of the particles of the various ingredients, the particular ingredients, and the like, mixing may take as little as 0.05h and usually not more than about 24h. In using a ball mill, certain parameters may be optimized. For example, the following equations may be used for rate of surface area production in $m^2/gh$:

$$rate=0.045/d+0.055D^{0.65}$$

$$rate=cpD^{1/2}bd^{-2}$$

$$rate=cpD^{1/2}bd^{-1}$$

where d is the media (ball) diameter, D is the mill diameter, p is the ball density, b is the particle diameter and c is a constant. It is generally argued that the milling rate varies directly with the diameter of the mill and inversely with the media diameter. Loading of the mill should be about 50% of the mill volume. The media should be as small as possible, but usually at least about 25 times the feed size. The feed should be at least about equal to the void volume between the media, preferably in slight excess. Mill rotation should be about 60–70% of critical speed $54.2/r^{1/2}$, where r is the radius of the mill in feet.

During the milling, walls may be scraped periodically to help promote milling/mixing. The media should be stable and inert under the conditions of the milling, various media being available, e.g., alumina, zirconia, tungsten carbide, boron carbide, etc.

In the case where the phosphoric acid source is milled with the calcium base source, the mixing will be continued until at least about 50% of the acid source has reacted to produce a partially neutralized mixture of calcium phosphate phase compounds, including amorphous calcium phosphates that may differ qualitatively from the initial ingredients.

It is found that a number of advantages ensue by having the intimate mixing with partial reaction occurring. First, the mixture when added to water usually does not go through intermediates which remove water as waters of hydration. Thus, less water needs to be added in order to provide for a workable mixture. The lower amount of water which must be added results in improved mechanical properties of the final product. In addition, the setting time is enhanced. In this way, one achieves a more stable product more quickly. This can be very important where the environment into which the composition is introduced may have a substantial amount of liquid, such as blood, which may be flowing and can modify the properties of the composition, as well as erode the composition away before it sets.

Once the mixture is formed it may be stored for long periods of time without change in composition or characteristics. Desirably, it is stored in a cold anhydrous environment in a vacuum, and a watertight container. If necessary, the product may be sterilized in accordance with conventional ways, using ethylene oxide, electron beam sterilization, gamma radiation, etc.

Alternatively, one may use a composition where the calcium source is mixed with the phosphoric acid, as described above, without milling. For example, one may combine finely divided bulk powders of tetracalcium phosphate and calcium carbonate in combination with the phosphoric acid. For example, a composition of interest includes from about 80 to 95% tetracalcium phosphate and 20 to 5% of calcium carbonate, particularly 90% and 10% respectively, based on calcium. The tetracalcium phosphate will generally be from about 1 to 30µ, usually 1–10µ, in size, while the calcium carbonate is usually up to 20µ in size, conveniently submicron, in size. For a description of the subject composition, see Table 1, Examples 1, 3, 4, 5, U.S. Ser. No. 588,890, filed Jul. 27, 1990, which disclosure is incorporated herein by reference.

The dry material will be combined with a physiologically acceptable lubricant, conveniently an aqueous lubricant, e.g., sterile water, comprising the base. If water is used, it will be substantially pure, such as double distilled, deionized or equivalent thereof. Other hydroxylic materials which are water miscible, pharmacologically acceptable and do not interfere with the calcium mineral formation, may also find use. For example, polyols, such as ethylene glycol, propylene glycol or glycerol may find use in minor amounts, less than about 10 volume percent.

When mixing with the lubricant, a wide variety of other materials may be employed. Various extenders may be employed, particularly grit or gravel of a particle size in the range of about 10 to 250µ, particularly with a filler composition. Desirably, the particles will be dense, sintered and be physiologically acceptable, particularly calcium phosphate particles. Of particular interest is dry calcium phosphate particles of from about 25 to 100µ in size. The amount of the particles or aggregate, when used, will generally be at least about 50 weight percent and not more than about 90 weight percent, usually not more than about 80 weight percent, and preferably from about 65 to 75 weight percent of the final mixture. The aggregate is selected so as to form a strong bond with the calcium phosphate matrix, enhance the compressive strength of the composition, and be physiologically acceptable.

In many situations, a wide variety of additives may be included in the medium to provide for specific properties. One group of additives is protein. Bone associated proteins may be added to modify the physical properties of the composition, enhance resorption, angiogenesis, cell entry and proliferation, mineralization, bone formation, growth of osteoclasts and/or osteoblasts, or the like. Proteins of particular interest are the different types of collagen, particularly Type I. Other proteins include osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor and skeletal growth factor. Other proteins associated with other parts of human or other mammalian anatomy, include proteins associated with cartilage, such as chondrocalcining protein; proteins associated with dentin, such as phosphophoryn, glycoproteins and Gla proteins; or proteins associated with enamel, such as amelognin and enamelin.

Structural proteins of interest include fibrin, fibrinogen, keratin, tubulin, elastin, and the like. Blood proteins may be employed, individually or together, in plasma or serum, e.g., serum albumin.

The protein may be combined with the acid source and/or the calcium source prior to milling or curing in a dried form so as to create intimate mixing and combination with the inorganic constituent of the cement. When added after milling, the proteins will generally vary from about 0.1 to 5, more usually 0.2 to 2 parts of protein based on calcium phosphate mineral, as an aqueous dispersion or solution. Usually, the protein will be present in from about 1 to 80 weight percent of the aqueous dispersion or solution. The protein dispersion will comprise the lubricant or be added in combination with the lubricant, where the total amount of water, if any, will come within the total amount of lubricant.

When the protein is added prior to milling, the mineral powders/crystals are weighed out and ground, e.g., with a mortar and pestle. The protein, e.g., collagen, is gradually and gently mixed into the mineral powder such that the mineral powders coat the protein material and the bulk volume of the protein is retained. The composite material is then gently ground while still maintaining the majority of the bulk volume of the composite. This composite material is placed into a mill jar with appropriate media loading for the bulk volume. After 2–4 hours, half the media needs to be removed adjusting to the decreasing bulk volume as ball milling progresses. The material is milled for about 8–24 hours.

Various other additives may be included to modify the physical structure of the final product. Various water soluble physiologically acceptable materials may be included, e.g., calcium carbonate, calcium sulfate, and NaCl (halite). Sugars, such as sucrose, glucose, or fructose may be included to enhance porosity. The weight of the soluble phase will usually not exceed 50 weight percent of the total solids.

The amount of lubricant which is used, will generally be from about 15 to 70, more usually from about 25 to 45 weight percent of the entire composition. Preferably, lower amounts of lubricant are used to provide for higher compressive strength and accompanying mechanical properties. The amount of lubricant which is used will be calculated in relation to the amount of water which is formed by reaction of the dry ingredients, so that in referring. to the total amount of lubricant, this will include the water produced by the reaction, as well as the lubricant added to the mixture.

The dry ingredients and the wet lubricating medium are combined and thoroughly mixed, so as to provide for a substantially uniform dispersion of the dry ingredients in the lubricant. Once the mixture is uniformly dispersed, it may then be mechanically dispersed, by kneading, rolling, sonicating, or the like. During the mixing, any gas which is formed should be released and the product may be shaped into any appropriate form. The mixing with the lubricant is over a relatively short time, usually not less than about 0.5 minutes and not more than about five minutes, usually not more than about 3 minutes. Where the product is to be introduced in situ, it may be injected into the appropriate site, which may be actively bleeding, using a syringe or catheter or packed in by other means, as appropriate.

The product is now allowed to set, during which time crystals grow and the product becomes a single integral mass. While the product may harden almost immediately, usually the maturing process should take at least about 2 min, usually about 8 min and not more than about 30 min, usually not more than about 25 min. Alternatively, where the material has been introduced at a site where it is to be retained, the material will naturally harden over time.

The physical properties of the final product may be varied, depending upon the particular ions which are used in the formation of the product. Microstructure may also be varied, since the shapes and size of the crystals can be varied with resulting variation in the mechanical and biological properties of the product. Also, bulk permeability may be changed in relation to the particular application, where a permeable or impermeable product is desired. The surface area of the reactant particles may also be modified where a high surface area may be desirable, for example, up to about 10 $m^2/gm$, to enhance protein binding, particularly charged proteins.

The subject products may be used for a variety of purposes, such as any form of connective tissue replacement, including bone cement, an injected prosthetic implant, a prosthetic orthopedic or dental implant, as a root canal filler, a prophylactic injection to augment weak osteoporotic bone, a hardware removal site filler, or a vehicle for drug delivery. The composition may be used as a paste, being applied to a surface for adherence or holding some structure in place.

The subject compositions may be used with other materials to provide for specific types of properties. Various additives may be employed which add additional tensile strength or fracture toughness, provide for enhanced flexibility, or the like. For example, fibrous materials may be employed, both organic and inorganic, such as silicon carbide whiskers, hydroxyapatite fibers, mineralized collagen fibers, metallic fibers, or the like. See, for example, U.S. Pat. No. 4,503,157.

Where a porous structure is desired, various additives may be included which may be leached out, so as to provide for porosity in the mixture, in addition to any porosity achieved with the release of gas formed during the reaction to produce the product. Aggregates of soluble materials above 25 volume percent will generally develop interconnected tunnels for bony ingrowth. Usually, the aggregate will be less than about 50 volume percent. Porosity may also be achieved by the particular anions and cations employed, where alkali metal salts are produced which are readily dissolved in the medium in which it is allowed to harden. Thus by adding calcium chloride and sodium or potassium hydroxide, the resulting salt will be water soluble and its dissolution will result in pathways through the structure. Similarly, one may include various water soluble fibers, particles, or the like, in the composite structure, which may also be leached out to provide for porosity. Thus, the method of preparation allows for varying the characteristics of the final product.

The viscosity of the product may be varied depending on the application. By varying the product composition, percentage of solids, and presence of other additives, the viscosity may be selected to allow for ease of administration to the site to be treated. By increasing the amount of lubricant in the paste, which occupies space in the final product, the loss of the lubricant will result in a void or pore. Use of flowable materials such as smectite clay (e.g., bentonite) may allow one to lower the amount of liquid, but leaves the clay in final product. Gas evolution from the face may also create voids in the crystallizing product. Thus, porosity may be controlled by adjusting the amount of lubricant and gas evolution.

When desired, very high compressive strengths may be achieved, usually in excess of 5000 psi (35 MPa), preferably in excess of 10,000 psi (75 MPa) and optimally in excess of 15,000 psi (110 MPa). Approximately 95% of final compressive strengths may be substantially achieved within fewer than about 8 hours, preferably fewer than about 4 hours. Time to one-half of the final compressive strength may be fewer than 5 hours, preferably fewer than 3 hours.

In addition, by having various proteins in the lubricant, the physical characteristics of the product will vary. When adding collagen to the paste, the crystallography of the final product is substantially unaffected, while the mechanical properties vary distinctively. The material appears viscoelastic, rather than having linear elasticity and brittleness, and appears to be more abrasion resistant. These properties indicate increased fracture toughness and resistance to fatigue.

As previously indicated, kits may be provided. The phosphate and/or carbonate sources may be provided as powders, which may be premixed or may be provided as separate solutions in appropriate amounts for mixing to provide the lubricant for the milled calcium phosphate mineral composition. The lubricant may be provided in a separate container, conveniently a syringe, where the syringe may be used to add the lubricant to the dry ingredients, the dry ingredients mixed and then taken up into the syringe for administration at the desired site.

The examples contained herein are offered by way of illustration and not by way of limitation.

EXPERIMENTAL

EXAMPLE 1

Measurement of Compression Strength

A compression die is coated with bovine serum and then packed with the test material. Packing may be achieved by finger packing, where the material is introduced into a cavity until the cavity is full, the material compacted with firm finger pressure and the cavity overfilled generously. In the case of a custom constant force spring-loader indention tester (garyometer), the material is inserted into all the cavities by any convenient means, and the material compressed with the Garyometer. The cavities are overfilled generously. The material is then smoothed over the top of the die until the material protrudes through the underside by at least 1 mm. The material is than cured while submerged in bovine serum in a plastic bag, where the bag is substantially freed of air. The sealed bag is than placed in a warm bucket of water in an incubator at 37° C. and allowed to set.

The die is removed from the water bath approximately 30 min prior to testing and the die rinsed generously with deionized water. The ends of the compression samples are then shaved to provide flush ends and the samples extracted from the mold employing a Delrin® plunger.

An Instron press is employed with appropriate recording charts. The first sample is placed on the platen and testing begun. The test is terminated just as the load starts to drop. Average compression strength is determined by the maximum pressure divided by cross-sectional area.

EXAMPLE 2

Effect of Single Solution on Functional Properties of Calcium Phosphate Cement Compression and set tests were carried out on 15.0 gram Norian cement samples comprised of 76.9 weight % hilgenstockite (tetracalcium phosphate, Ca4(PO4)20, monoclinic, $P2_1$), 9.3 weight % calcite (calcium carbonate, CaCO3, hexagonal-R, R3bar/c), and 13.7 weight % orthophosphoric acid (H3PO4, monoclinic, $P2_1/c$) to establish the effects of differing solution concentration and species.

Bases (hilgenstockite and calcite) were mixed together in a mortar and pestle for 15 seconds, followed by acid which was mixed for 30 seconds, and the solution which was mixed for 3 minutes.

An "off the shelf" buffer solution (Sigma Diagnostics 1.0 M Phosphate Buffer) was diluted with deionized water to furnish solutions at 0.5 M, 0.25 M, and 0.15 M ionic concentrations. Sigma Diagnostics 1.0 M and 0.1 M Phosphate Buffers were used "straight from the bottle". Phosphate buffer solutions were used to determine set time, as described below. Dibasic sodium phosphate solutions of 0.1 M, 0.15 M, and 0.2 M concentration were used to measure both set and strength values.

Strength testing was carried out as described in Example 1, above. Set tests were carried out by placing freshly mixed cement pellets of a given size in serum at 37° C. Samples were periodically tested by lowering a probe (Gillmore needle with 0.25 lb weight) to the sample surface, to establish the time at which an indentation was not visible (set time).

Functional test results are summarized below:
PO4 buffer solution, liquid/solid ratio=0.46

| Molarity (mol/l) | Ave. Set Time (min) |
|---|---|
| 0.1 | 12 |
| 0.15 | 9 |
| 0.25 | 6 |
| 0.5 | 4 |
| 1.0 | 4 |

Na2HPO4 solution, liquid/solid raio=0.47

| | | Strength (MPa) | |
|---|---|---|---|
| Molarity (mol/l) | Ave. Set (min) | fingerpack | garyometer |
| colloid (control)* | 16 | 17.3 ± 2.1 | 23.9 ±1.4 |
| 0.1 | 11.5 | 17.9 ± 1.9 | 32.1 ± 1.9 |
| 0.15 | 8 | 25.7 ± 1.5 | 27.1 ± 1.7 |
| 0.2 | 7.5 | — | — |

EXAMPLE 3

Solution Effect on Set 15.0 gram cement samples of the composition described in Example 2 were mixed, using a number of different solutions at ionic strengths of 0.3 M and 0.03 M. These cement mixtures were tested for set time, as described in Example 2, above.

Functional test results are summarized below:

| | Set time (min.) | |
|---|---|---|
| Solution Species | 0.03 Molar | 0.3 Molar |
| Colloid (control)* | | 15 |
| deionized H20 | >16 (ionic Strength = 0) | |
| $Na_2CO_3.H_2O$ | | 4 |
| $NaHCO_3$ | | 6 |
| $Na_3PO_4.12H_2O$ | | 6 |
| $Na_2HPO_4$ | 10 | 7 |
| $NaH_2PO_4.H_2O$ | 16 | 4 |
| $H_3PO_4$ | | 12 |

*Colloid Preparation

The following is illustrative of the colloid preparation with a particular molarity of calcium and phosphate. A 0.30 M sodium phosphate solution is prepared by combining 0.5704 g of trisodium phosphate dodecahydrate and 0.04024 g of dibasic solium phosphate heptahydrate and dissolved in deionized water to provide the proper molarity. A 0.50 M calcium chloride solution is prepared by dissolving 0.0736 g of calcium chloride dihydrate in the appropriate amount of deionized water and the mixture stirred for 15 min. The solutions may then be combined immediately prior to use to provide the desired colloid solution.

The methods and compositions according to the present invention permit one to substantially enhance setting times and provide for high compressive strength products as appropriate, by adding phosphate or carbonate compositions in solution. Thus, one may provide freshly prepared calcium phosphate minerals for various physiological purposes, where the products set up without significant deterioration from the presence of the blood during the procedure. In this manner, one can introduce strong, relatively long lived structures into the body to provide the necessary stability and support required for fillers, prosthetic devices and the like.

All publications and patent applications mentioned in this specification are herein incorporated by reference to the same extent as if each individual publication or patent application was specifically and. individually indicated to be incorporated by reference.

The invention now being fully described, it will be apparent to one of ordinary skill in the art that many changes and modifications can be made thereto without departing from the spirit or scope of the appended claims.

What is claimed is:

1. A kit for preparing a calcium phosphate mineral, said kit consisting of:
   at least one calcium source and at least one phosphate source as dry ingredients; and
   a solution, wherein said solution consists of water and a solute selected from the group consisting of a sodium phosphate and a sodium carbonate;
   wherein said dry ingredients and solution are present in separate containers.

2. The kit according to claim 1, wherein said solute is a sodium phosphate.

3. The kit according to claim 1, wherein said solute is a sodium carbonate.

4. A kit for preparing a calcium phosphate mineral, said kit consisting of:
   at least one calcium source and at least one phosphoric acid source free of uncombined water as dry ingredients; and
   a solution consisting of water and a sodium phosphate;
   wherein said dry ingredients and solution are present in separate containers.

5. The kit according to claim 4, wherein said sodium phosphate is present in said water at a concentration ranging from 0.01 to 2 M.

6. The kit according to claim 4, wherein said solution has a pH in the range of about 6 to 11.

7. The kit according to claim 4, wherein said dry ingredients are premixed.

8. A kit for preparing a calcium phosphate mineral, said kit consisting of:
   at least one calcium source and at least one phosphoric acid source free of uncombined water as dry ingredients; and
   a solution consisting of water and a sodium phosphate, where the concentration of said sodium phosphate in said water ranges from 0.01 to 2.0 M and said solution has a pH in the range of about 6 to 11.

9. The kit according to claim 8, wherein said sodium phosphate is present in said water at a concentration ranging from about 0.05 to 0.5 M.

10. The kit according to claim 8, wherein said solution has a pH in the range from about 7 to 9.

* * * * *